United States Patent
Meng (10) Patent No.: US 10,479,810 B2
(45) Date of Patent: Nov. 19, 2019

(54) CRYSTAL FORM OF TENOFOVIR ALAFENAMIDE SALT, PREPARATION METHOD AND USE THEREOF

(71) Applicant: SHANGHAI BEGREAT PHARMATECH, Shanghai (CN)

(72) Inventor: Xiaoming Meng, Tianjin (CN)

(73) Assignee: SHANGHAI BEGREAT PHARMATECH, Shanghai (CN)

( * ) Notice: Subject to any disclaimer, the term of this patent is extended or adjusted under 35 U.S.C. 154(b) by 0 days.

(21) Appl. No.: 16/208,721

(22) Filed: Dec. 4, 2018

(65) Prior Publication Data

US 2019/0100542 A1   Apr. 4, 2019

Related U.S. Application Data

(63) Continuation of application No. PCT/CN2017/088538, filed on Jun. 15, 2017.

(30) Foreign Application Priority Data

Jun. 5, 2016  (CN) .......................... 2016 1 0402175

(51) Int. Cl.
| | |
|---|---|
| *C07F 9/6561* | (2006.01) |
| *A61K 31/675* | (2006.01) |
| *A61P 31/20* | (2006.01) |
| *A61P 31/18* | (2006.01) |

(52) U.S. Cl.
CPC ........ *C07F 9/65616* (2013.01); *A61K 31/675* (2013.01); *A61P 31/18* (2018.01); *A61P 31/20* (2018.01); *C07B 2200/13* (2013.01)

(58) Field of Classification Search
None
See application file for complete search history.

(56) References Cited

U.S. PATENT DOCUMENTS

| | | |
|---|---|---|
| 2005/0159392 A1 | 7/2005 | Becker et al. |
| 2014/0187773 A1 | 7/2014 | Liu et al. |

FOREIGN PATENT DOCUMENTS

| | | |
|---|---|---|
| CN | 104817593 A | 8/2015 |
| CN | 105085571 A | 11/2015 |
| WO | 2013025788 A1 | 2/2013 |

OTHER PUBLICATIONS

International Search Report in PCT/CN2017/088538 dated Sep. 15, 2017, 5 pages.

*Primary Examiner* — Samantha L Shterengarts
(74) *Attorney, Agent, or Firm* — Metis IP LLC (57) ABSTRACT

Disclosed are a new polymorph II, crystal form A and B of 9-[(R)-2-[[(S)-[[(S)-1-(isopropoxycarbonyl)ethyl]amino] phenoxyphosphinyl]methoxy]propyl]adenine fumarate, and preparation methods and pharmaceutical use thereof. The crystal form II is a hemi-fumarate; the crystal form A is a mono-fumarate; and the crystal form B is a sesqui-fumarate. Compared with the existing crystal form, the new crystal forms have obvious advantages in solubility, stability and preparation process.

20 Claims, 5 Drawing Sheets

CRYSTAL FORM OF TENOFOVIR ALAFENAMIDE SALT, PREPARATION METHOD AND USE THEREOF

CROSS-REFERENCE TO RELATED APPLICATIONS

This application is a continuation of International Application No. PCT/CN2017/088538, filed on Jun. 15, 2017, which claims priority to Chinese Application No. 201610402175.4, filed on Jun. 5, 2016. The above-referenced applications are incorporated herein by reference in their entirety.

TECHNICAL FIELD

The present invention relates to novel crystals of 9-[(R)-2-[[(S)-[[(S)-1-(isopropoxycarbonyl)ethyl]amino]phenoxyphosphinyl]methoxy]prop yl]adenine fumarate and its preparation method and use.

BACKGROUND

Compound 1, tenofovir alafenamide (TAF or GS-7340) is one of the main ingredients in the FDA-approved anti-AIDS drug Genvoya. The drug was developed by Gilead. Tenofovir alafenamide is a nucleic acid reverse transcriptase inhibitor and a potential drug for tenofovir.

The formula of tenofovir alafenamide is $C_{21}H_{29}N_6O_5P$, which has a molecular weight of 467.5. The chemical structural formula of tenofovir alafenamide is as follows:

Chemical raw materials of active pharmaceutical ingredients (API) must have good purity, stability, physical and chemical properties and operability. These properties are related to the crystalline Form of the drug, and different crystal Forms have different physical and chemical properties. The purpose of improving the stability of the drug preservation and the efficacy of the drug, it is necessary to make the raw API into crystal Form.

A drug may exist in a plurality of crystalline Forms, and different crystal Forms of the same drug may have different dissolution and absorption in the body, thereby affecting the dissolution and release of the Formulation.

The optimal crystalline Form can be discovered by thoroughly studying of the polymorphism of the compound. The optimal crystalline Form is crucial to the efficacy of the drug and the Formulation process which is based on the characteristics of the crystalline Form, thereby effectively ensuring the equivalence of the drug batch to batch.

The physicochemical properties of the pharmaceutically active substance can be improved by selecting the form of its appropriate salt: such as solubility, dissolution rate, stability, purity, and the like. These physical and chemical properties further influence the quality and bioavailability of the drug. However, the choice of counter ion pairs used for salt formation and the formation of salts are not always straightforward, as the physical and chemical properties of different counter ions forming salts with the same compounds can vary widely. Some of salts can improve physical and chemical properties while some salt cannot be improved. Sometimes, the salt even has the poor physical and chemical properties. Therefore, finding and manufacturing a salt for pharmaceutically developable and improving the physical properties of a drug is a practical creation work.

A drug and a salt thereof may exist in a plurality of crystalline form states, and different crystal forms of the same drug and its salt may have different dissolution and absorption in the body, thereby affecting dissolution and release of the preparation.

The research on the polymorphic form of the drug and its salt can find the optimal crystalline form of the drug which is beneficial to the action of the drug, and at the same time, determine the formulation process according to the characteristics of the crystalline form, and effectively ensure the equivalence of the batch drug in the production.

Tenofovir alafenamide hemifumarate is one of the main components of the anti-AIDS drug Genvoya. The Genovya combination also contains other drugs such as Elvitegravir, cobicistat, emtricitabine. In the current technology, when TAF hemifumarate crystal form I (WO2013025788A1) is mixed with emtricitabine to form a tablet, the chemical stability of TAF is affected, and degradation products are easily generated, thereby affecting the quality and efficacy of the combination formulation. In order to solve this difficult problem, we have unexpectedly discovered that the new crystalline form II, monofumarate (form A) and sesquifumarate (form B) of TAF can significantly improve the chemical compatibility of TAF with emtricitabine, which makes this comb formulation more stable and improves quality and shelf life.

SUMMARY

A crystalline Form of 9-[(R)-2-[[(S)-[[(S)-1-(isopropoxycarbonyl)ethyl]amino]phenoxyphosphinyl]methoxy]prop yl]adenine fumarate designated as Form II, having an X-ray powder diffraction pattern comprising diffraction peaks at 2θ values: 26.6±0.2, 21.3±0.2, 27.1±0.2, 19.6±0.2, 18.7±0.2. Preferably, wherein the X-ray powder diffraction pattern further comprises the following 2θ values: 32.1±0.2, 21.9±0.2, 5.4±0.2, 22.4±0.2, 11.1±0.2, 17.8±0.2. Preferably, wherein the X-ray powder diffraction pattern further comprises the following 2θ values: 15.9±0.2, 24.5±0.2, 24.9±0.2, 19.0±0.2, 23.6±0.2, 30.0±0.2. Preferably, wherein the X-ray powder diffraction pattern further comprises the following 2θ values: 32.4±0.2, 37.5±0.2, 10.5±0.2, 14.5±0.2, 16.7±0.2, 40.3±0.2. More preferably, wherein the X-ray powder diffraction pattern further comprises the following 2θ values: 23.9±0.2, 12.3±0.2, 38.6±0.2, 43.0±0.2, 27.8±0.2, 35.8±0.2.

The melting point of 9-[(R)-2-[[(S)-[[(S)-1-(isopropoxycarbonyl)ethyl]amino]phenoxyphosphinyl]methoxy]prop yl]adenine fumarate Form II is 106.6±2° C.

A process for the preparation of 9-[(R)-2-[[(S)-[[(S)-1-(isopropoxycarbonyl)ethyl]amino]phenoxyphosphinyl]methoxy]prop yl]adenine fumarate Form II comprising:
(i) 9-[(R)-2-[[(S)-[[(S)-1-(isopropoxycarbonyl)ethyl]amino]phenoxyphosphinyl]methoxy]prop yl]adenine free base was dissolved in organic solution.

(ii) Added aliquot fumaric acid into the solution prepared in process (i) to make precipitation of the fumarate salt.
(iii) 9-[(R)-2-[[(S)-[[(S)-1-(isopropoxycarbonyl)ethyl]amino]phenoxyphosphinyl]methoxy]prop yl]adenine fumarate form II was obtained after liquid-solid separation.

A crystalline Form of 9-[(R)-2-[[(S)-[[(S)-1-(isopropoxycarbonyl)ethyl]amino]phenoxyphosphinyl]methoxy]prop yl]adenine fumarate designated as Form A, having an X-ray powder diffraction pattern comprising diffraction peaks at 2θ values: 23.8±0.2, 10.5±0.2, 28.5±0.2, 21.2±0.2, 19.5±0.2. Preferably, wherein the X-ray powder diffraction pattern further comprises the following 2θ values: 15.1±0.2, 23.2±0.2, 17.0±0.2, 9.8±0.2, 20.8±0.2, 17.6±0.2. Preferably, wherein the X-ray powder diffraction pattern further comprises the following 2θ values: 15.7±0.2, 27.1±0.2, 25.2±0.2, 33.5±0.2, 22.4±0.2, 19.0±0.2. Preferably, wherein the X-ray powder diffraction pattern further comprises the following 2θ values: 13.3±0.2, 4.8±0.2, 9.6±0.2, 26.7±0.2, 5.3±0.2, 11.4±0.2. More preferably, wherein the X-ray powder diffraction pattern further comprises the following 2θ values: 14.0±0.2, 30.2±0.2, 8.5±0.2, 31.3±0.2, 21.9±0.2, 12.5±0.2.

A process for the preparation of 9-[(R)-2-[[(S)-[[(S)-1-(isopropoxycarbonyl)ethyl]amino]phenoxyphosphinyl]methoxy]prop yl]adenine fumarate Form A:
(i) 9-[(R)-2-[[(S)-[[(S)-1-(isopropoxycarbonyl)ethyl]amino]phenoxyphosphinyl]methoxy]prop yl]adenine free base was dissolved in organic solution.
(ii) Added excessive fumaric acid into the solution prepared in process (i) to make precipitation of the fumarate salt.
(iii) 9-[(R)-2-[[(S)-[[(S)-1-(isopropoxycarbonyl)ethyl]amino]phenoxyphosphinyl]methoxy]prop yl]adenine fumarate form A was obtained after liquid-solid separation.

A crystalline Form of 9-[(R)-2-[[(S)-[[(S)-1-(isopropoxycarbonyl)ethyl]amino]phenoxyphosphinyl]methoxy]prop yl]adenine fumarate designated as Form B, having an X-ray powder diffraction pattern comprising diffraction peaks at 2θ values: 10.5±0.2, 21.0±0.2, 10.9±0.2, 27.2±0.2, 22.5±0.2. Preferably, wherein the X-ray powder diffraction pattern further comprises the following 2θ values: 28.9±0.2, 27.7±0.2, 24.1±0.2, 18.7±0.2, 13.5±0.2, 20.6±0.2. Preferably, wherein the X-ray powder diffraction pattern further comprises the following 2θ values: 4.9±0.2, 14.1±0.2, 11.2±0.2, 16.4±0.2, 23.3±0.2, 19.6±0.2. Preferably, wherein the X-ray powder diffraction pattern further comprises the following 2θ values: 14.8±0.2, 15.1±0.2, 12.3±0.2, 38.0±0.2, 17.3±0.2, 15.7±0.2. More preferably, wherein the X-ray powder diffraction pattern further comprises the following 2θ values: 18.1±0.2, 21.8±0.2, 31.8±0.2, 35.0±0.2, 41.7±0.2, 40.0±0.2.

A process for the preparation of 9-[(R)-2-[[(S)-[[(S)-1-(isopropoxycarbonyl)ethyl]amino]phenoxyphosphinyl]methoxy]prop yl]adenine fumarate Form B comprising:
(i) 9-[(R)-2-[[(S)-[[(S)-1-(isopropoxycarbonyl)ethyl]amino]phenoxyphosphinyl]methoxy]prop yl]adenine free base was dissolved in organic solution.
(ii) Added excessive fumaric acid into the solution prepared in process (i) to make precipitation of the fumarate salt.
(iii) 9-[(R)-2-[[(S)-[[(S)-1-(isopropoxycarbonyl)ethyl]amino]phenoxyphosphinyl]methoxy]prop yl]adenine fumarate form B was obtained after liquid-solid separation.

A pharmaceutical composition comprising the crystal Forms A, B and II as an active ingredient.

A pharmaceutical composition comprising the crystal Forms including Form A, B and II as an active ingredient for treatment of virus-related diseases.

The treatment of a virus-related disease. The disease is selected from: hepatitis B virus (HBV) and/or human immunodeficiency virus (HIV) infection.

EXAMPLES

The specific embodiments of the present invention are further described in detail below with reference to the drawings and embodiments. The following examples are intended to illustrate the invention, but are not intended to limit the scope of the invention.

The X-ray powder diffraction operation and analysis steps in this present disclosure are as follows:

The Rigaku Ultima IV powder diffractometer was used, which was irradiated with Cu—K(R) (40 kV, 40 mA) at room temperature using a D/tex Ultra detector. The scanning range is from 3° to 45° in the 2θ interval, and the scanning speed is 20°/min.

Measurement differences associated with X-ray powder diffraction analysis results are produced by a variety of factors including: (a) errors in sample preparation (e.g., sample height), (b) instrument error, (c) calibration differences, (d) operator error (including errors that occur when determining peak position), and (e) properties of the substance (e.g., preferred orientation error). Calibration errors and sample height errors often result in displacement of all peaks in the same direction. When using a flat sampler, small differences in sample height will result in large displacements of the XRPD peak position. Systematic studies have shown that a 1 mm sample height difference can result in a 2θ peak shift of up to 10. These displacements can be identified from the X-ray diffraction pattern and can be eliminated by compensating for the displacement (using a system calibration factor for all peak position values) or recalibrating the instrument. As described above, the measurement errors from different instruments can be corrected by applying a system calibration factor to make the peak positions consistent.

A differential scanning calorimetry (DSC) analysis was performed on the crystal Forms in Examples, using a TA Q2000 differential scanning calorimeter using an $N_2$ atmosphere at a temperature rising rate of 10° C./min.

The thermogravimetric (TGA) analysis of the crystal Forms in Examples was carried out using a TA Q500 thermogravimetric analyzer using a $N_2$ atmosphere at a heating rate of 10° C./min.

Example 1

50 mg of 9-[(R)-2-[[(S)-[[(S)-1-(isopropoxycarbonyl)ethyl]amino]phenoxyphosphinyl]methoxy]prop yl]adenine freebase was slurried in 1 ml alcohol organic solvent and then 0.5-1 aliquots of fumaric acid was added and the precipitation was obtained.

The alcohol organic solvent is selected from: Methanol, ethanol, n-propanol, isopropanol, n-butanol, isobutanol, n-octanol and 2,2,2-trifluoroethanol.

Figure 1:
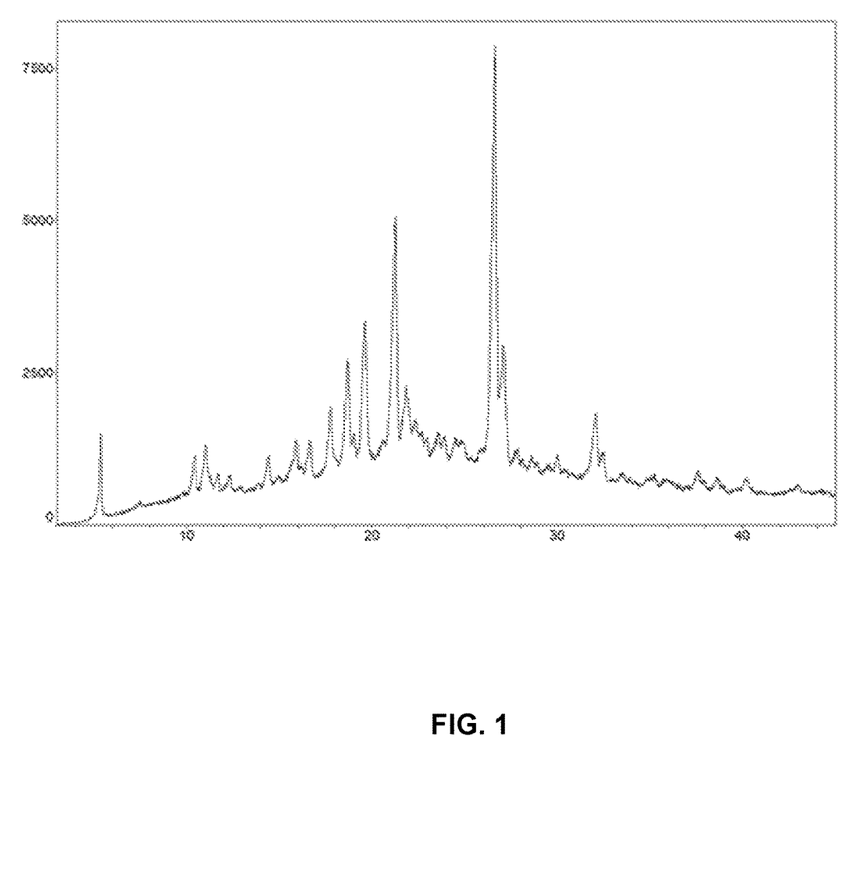
FIG. 1 is an XRPD diffraction pattern of 9-[(R)-2-[[(S)-[[(S)-1-(isopropoxycarbonyl)ethyl]amino]phenoxyphosphinyl]methoxy]prop yl]adenine fumarate Form II. 2θ values in unit of degree in accordance with the abscissa. The intensity of diffraction peak as ordinate.

The XRPD pattern of the resulting crystal Form II is shown in FIG. 1 and information of diffraction peaks at 2θ values was list in the following table:

| 2θ (degree) | d(Å) | I(Height) % |
|---|---|---|
| 5.397 | 16.3618 | 13.6 |
| 7.478 | 11.812 | 1.3 |
| 10.476 | 8.4371 | 5.2 |
| 11.060 | 7.9931 | 12.2 |
| 11.734 | 7.5356 | 2.7 |
| 12.302 | 7.1887 | 3.5 |
| 12.942 | 6.8347 | 0.4 |
| 14.457 | 6.1218 | 4.9 |
| 15.003 | 5.9003 | 1.4 |
| 15.903 | 5.5683 | 9.6 |
| 16.661 | 5.3165 | 4.8 |
| 17.798 | 4.9793 | 11.6 |
| 18.700 | 4.7412 | 20.3 |
| 19.022 | 4.6616 | 7.9 |
| 19.619 | 4.5212 | 27.6 |
| 21.260 | 4.1757 | 45.4 |
| 21.859 | 4.0626 | 15.4 |
| 22.360 | 3.9727 | 12.6 |
| 22.708 | 3.9126 | 1.1 |
| 23.009 | 3.8622 | 0.7 |
| 23.560 | 3.773 | 7.2 |
| 23.902 | 3.7198 | 4.1 |
| 24.520 | 3.6275 | 8.3 |
| 24.899 | 3.573 | 8.1 |
| 26.640 | 3.3433 | 100 |
| 27.100 | 3.2877 | 35.6 |
| 27.782 | 3.2085 | 3.2 |
| 28.603 | 3.1182 | 2.8 |
| 28.918 | 3.0849 | 2.1 |
| 29.577 | 3.0177 | 2.2 |
| 30.018 | 2.9744 | 6.5 |
| 30.417 | 2.9363 | 0.4 |
| 32.060 | 2.7894 | 19.6 |
| 32.440 | 2.7577 | 5.5 |
| 33.555 | 2.6685 | 2.8 |
| 33.875 | 2.644 | 0.6 |
| 34.820 | 2.5744 | 2.9 |
| 35.243 | 2.5444 | 2.9 |
| 35.781 | 2.5075 | 3 |
| 37.541 | 2.3938 | 5.3 |
| 37.918 | 2.3709 | 2.2 |
| 38.620 | 2.3294 | 3.5 |
| 40.277 | 2.2373 | 4.7 |
| 42.982 | 2.1026 | 3.4 |

A differential scanning calorimetry (DSC) analysis was performed on the crystal Form II in Example 1, using a TA Q2000 differential scanning calorimeter using an $N_2$ atmosphere at a temperature rising rate of 10° C./min. The DSC plot of Form II is shown in FIG. 2.

The thermogravimetric (TGA) analysis of the crystal Form II in Example 1 was carried out using a TA Q500 thermogravimetric analyzer using a $N_2$ atmosphere at a heating rate of 10° C./min. The TGA plot of Form II is shown in FIG. 3.

Figure 2:
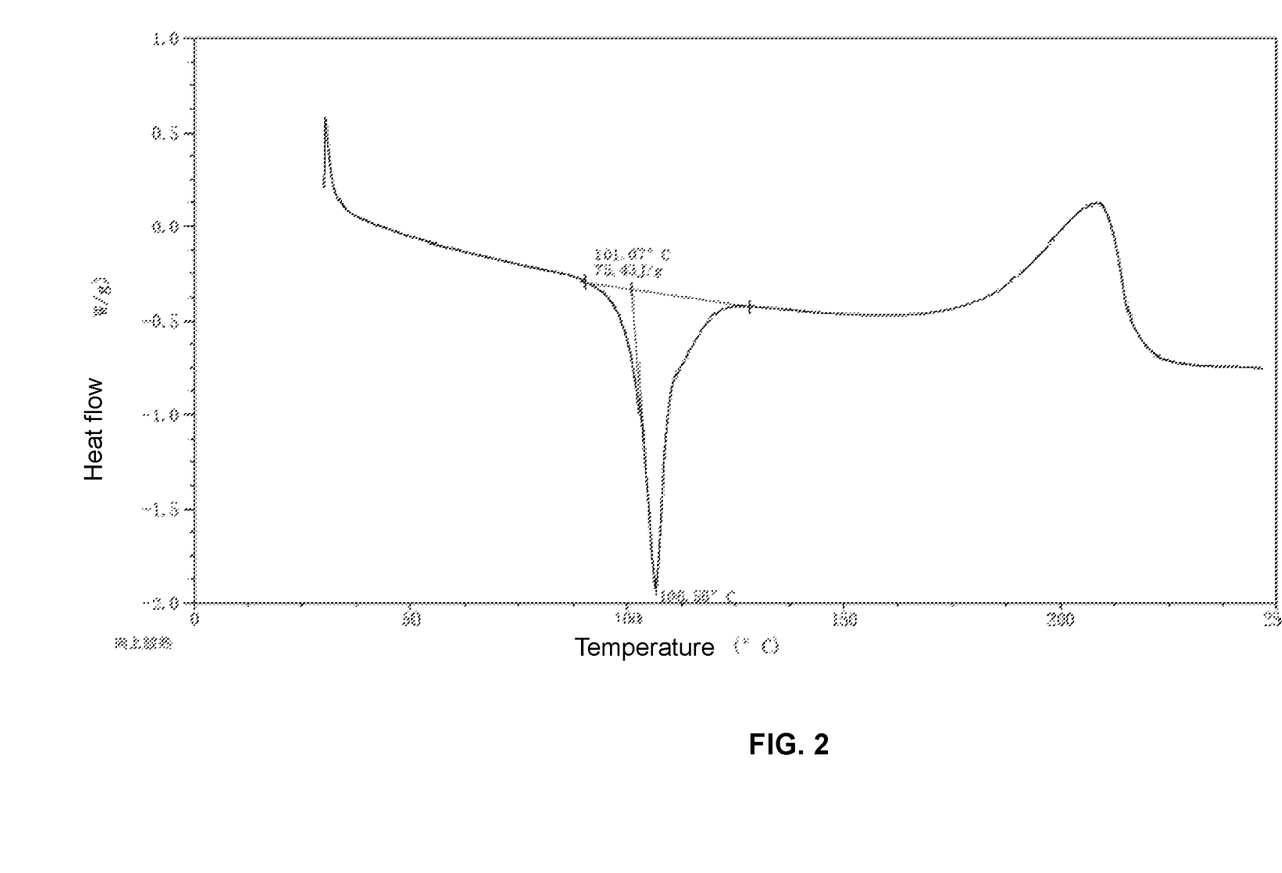
FIG. 2 is a DSC plot of 9-[(R)-2-[[(S)-[[(S)-1-(isopropoxycarbonyl)ethyl]amino]phenoxyphosphinyl]methoxy]prop yl]adenine fumarate Form II. Temperature in unit of ° C. in accordance with the abscissa. The Heat flow (w/g) as ordinate.
Figure 3:
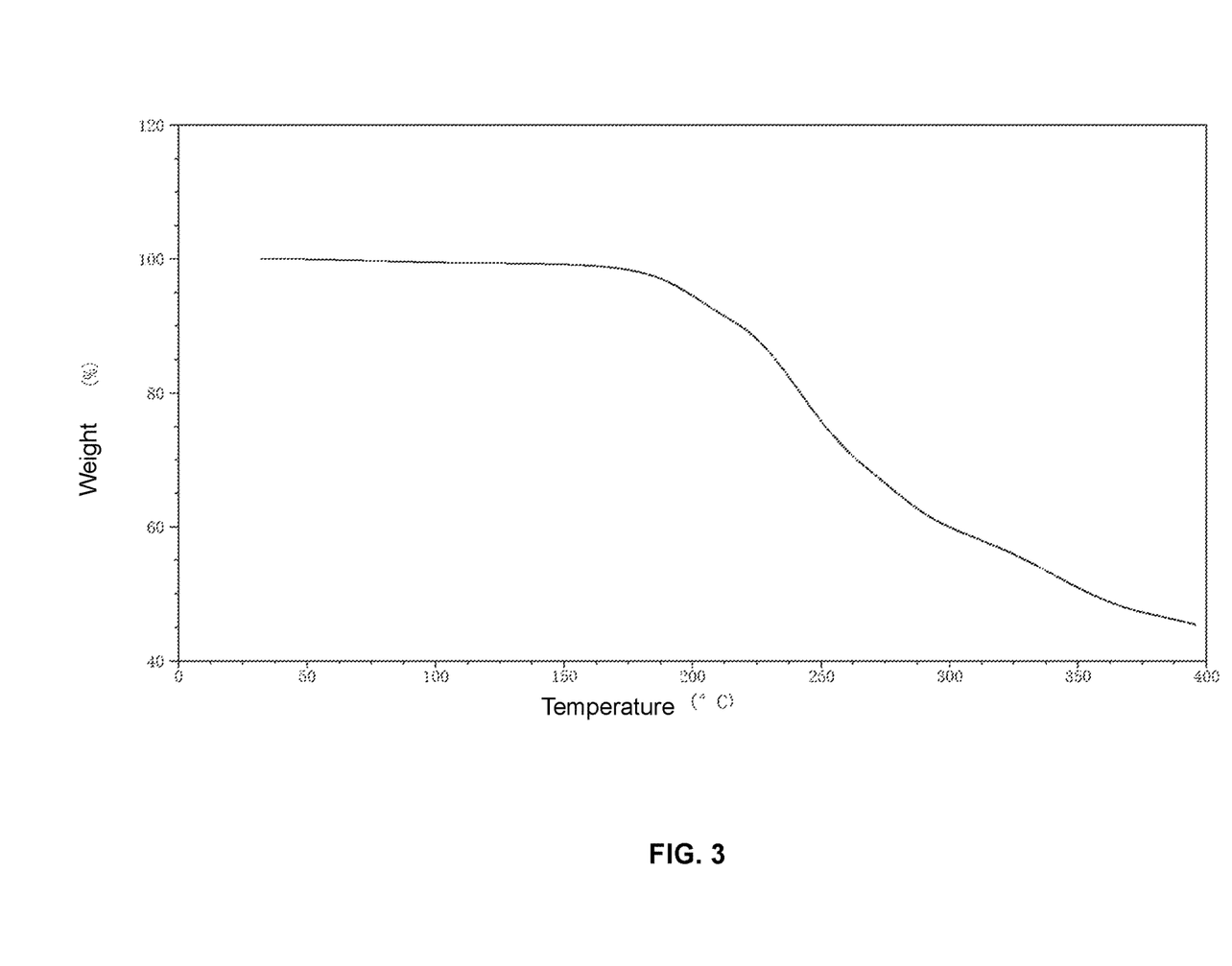
FIG. 3 is a TGA plot of 9-[(R)-2-[[(S)-[[(S)-1-(isopropoxycarbonyl)ethyl]amino]phenoxyphosphinyl]methoxy]prop yl]adenine fumarate Form II. Temperature in unit of ° C. in accordance with the abscissa. The Weight (%) as ordinate.

The DSC pattern of Form II is shown in FIG. 2, and the TGA pattern of Form II is shown in FIG. 3. FIG. 2 shows that the peak melting point of Form II is 106.56° C. FIG. 3 shows that no significant weight loss was observed before heating to 160° C., indicating that Form II was an anhydrate.

Example 2

50 mg of 9-[(R)-2-[[(S)-[[(S)-1-(isopropoxycarbonyl)ethyl]amino]phenoxyphosphinyl]methoxy]prop yl]adenine freebase was slurried in 1 ml chlorinated alkane organic solvent and then 0.5-1 aliquots of fumaric acid was added and the precipitation was obtained. The precipitation was allowed to be slurried for 24 hours. The XRPD pattern of the obtained Form II is consistent with FIG. 1.

The chlorinated alkane organic solvent is selected from: Dichloromethane, chloroform and 1,2-dichloroethane.

Example 3

50 mg of 9-[(R)-2-[[(S)-[[(S)-1-(isopropoxycarbonyl)ethyl]amino]phenoxyphosphinyl]methoxy]prop yl]adenine freebase was slurried in 1 ml ester organic solvent and then 0.5-1 aliquots of fumaric acid was added and the precipitation was obtained. The precipitation was allowed to be slurried for 24 hours. The XRPD pattern of the obtained Form II is consistent with FIG. 1.

The ester organic solvent is selected from: Ethyl formate, ethyl acetate, isopropyl acetate, butyl acetate and dimethyl carbonate.

Example 4

50 mg of 9-[(R)-2-[[(S)-[[(S)-1-(isopropoxycarbonyl)ethyl]amino]phenoxyphosphinyl]methoxy]prop yl]adenine freebase was slurried in 1 ml ketone organic solvent and then 0.5-1 aliquots of fumaric acid was added and the precipitation was obtained. The precipitation was allowed to be slurried for 24 hours. The XRPD pattern of the obtained Form II is consistent with FIG. 1.

The ketone organic solvent is selected from: Acetone, 2-butanone, 3-pentanone, 4-methyl-2-pentanone.

Example 5

50 mg of 9-[(R)-2-[[(S)-[[(S)-1-(isopropoxycarbonyl)ethyl]amino]phenoxyphosphinyl]methoxy]prop yl]adenine freebase was slurried in 1 ml aromatic hydrocarbon organic solvent and then 0.5-1 aliquots of fumaric acid was added and the precipitation was obtained. The precipitation was allowed to be slurried for 24 hours. The XRPD pattern of the obtained Form II is consistent with FIG. 1.

The aromatic hydrocarbon organic solvent is selected from: Toluene, cumene, p-xylene, mesitylene and chlorobenzene.

Example 6

50 mg of 9-[(R)-2-[[(S)-[[(S)-1-(isopropoxycarbonyl)ethyl]amino]phenoxyphosphinyl]methoxy]prop yl]adenine freebase was slurried in 1 ml ether organic solvent and then 0.5-1 aliquots of fumaric acid was added and the precipitation was obtained. The precipitation was allowed to be slurried for 24 hours. The XRPD pattern of the obtained Form II is consistent with FIG. 1.

The ether organic solvent is selected from: Ether, diisopropyl ether, methyl tert-butyl ether, methyl cyclopentyl ether.

Example 7

50 mg of 9-[(R)-2-[[(S)-[[(S)-1-(isopropoxycarbonyl) ethyl]amino]phenoxyphosphinyl]methoxy]prop yl]adenine freebase was slurried in 1 ml alkane organic solvent and then 0.5-1 aliquots of fumaric acid was added and the precipitation was obtained. The precipitation was allowed to be slurried for 24 hours. The XRPD pattern of the obtained Form II is consistent with FIG. 1.

The alkane organic solvent is selected from: n-hexane, cyclohexane, n-heptane.

Example 8

50 mg of 9-[(R)-2-[[(S)-[[(S)-1-(isopropoxycarbonyl) ethyl]amino]phenoxyphosphinyl]methoxy]prop yl]adenine freebase was slurried in 1 ml acetonitrile organic solvent and then 0.5-1 aliquots of fumaric acid was added and the precipitation was obtained. The precipitation was allowed to be slurried for 24 hours. The XRPD pattern of the obtained Form II is consistent with FIG. 1.

Example 9

50 mg of 9-[(R)-2-[[(S)-[[(S)-1-(isopropoxycarbonyl) ethyl]amino]phenoxyphosphinyl]methoxy]prop yl]adenine freebase was slurried in 1 ml nitromethane organic solvent and then 0.5-1 aliquots of fumaric acid was added and the precipitation was obtained. The precipitation was allowed to be slurried for 24 hours. The XRPD pattern of the obtained Form II is consistent with FIG. 1.

Example 10

50 mg of 9-[(R)-2-[[(S)-[[(S)-1-(isopropoxycarbonyl) ethyl]amino]phenoxyphosphinyl]methoxy]prop yl]adenine freebase was slurried in 1 ml 1,4-dioxane organic solvent and then 0.5-1 aliquots of fumaric acid was added and the precipitation was obtained. The precipitation was allowed to be slurried for 24 hours. The XRPD pattern of the obtained Form II is consistent with FIG. 1.

Example 11

50 mg of 9-[(R)-2-[[(S)-[[(S)-1-(isopropoxycarbonyl) ethyl]amino]phenoxyphosphinyl]methoxy]prop yl]adenine freebase was slurried in 1 ml 3-methyl-1-butanol organic solvent and then excessive aliquots of fumaric acid was added and the precipitation was obtained. The precipitation was allowed to be slurried for 24 hours. The XRPD pattern of the obtained Form A is consistent with FIG. 4.

Figure 4:
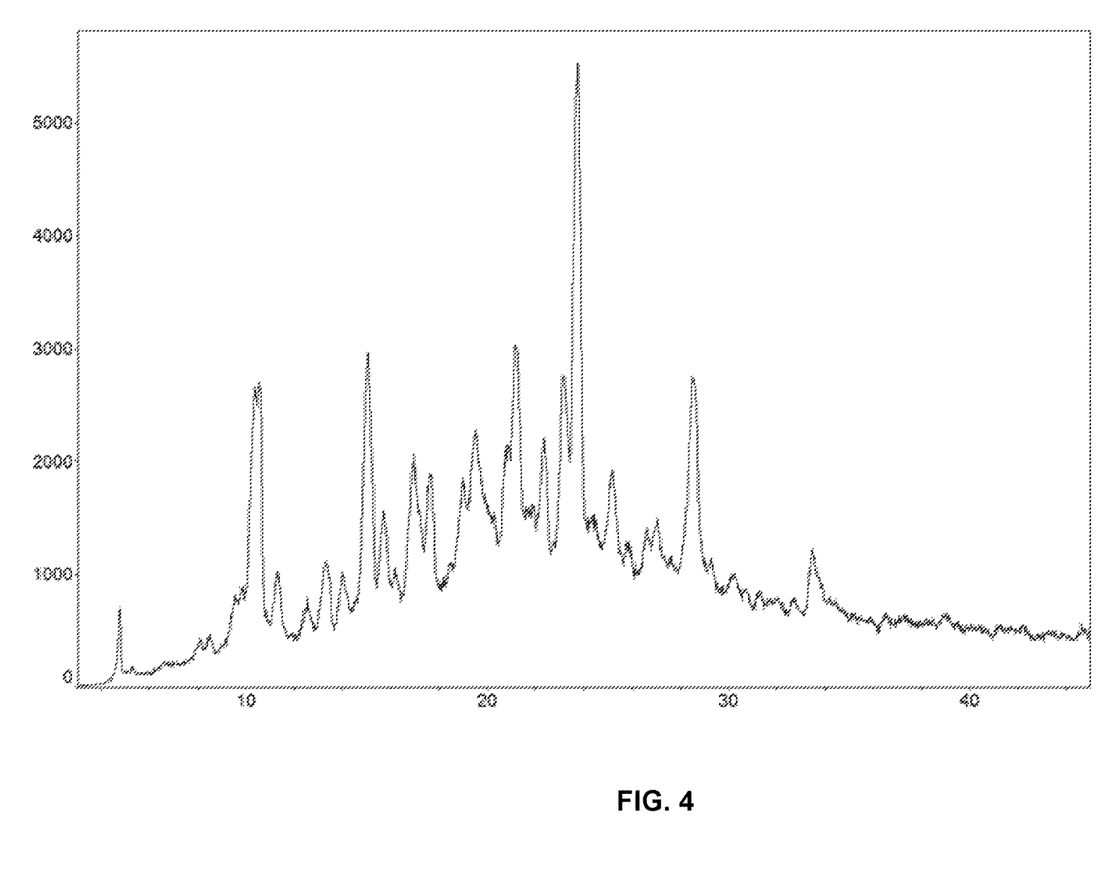
FIG. 4 is an XRPD diffraction pattern of 9-[(R)-2-[[(S)-[[(S)-1-(isopropoxycarbonyl)ethyl]amino]phenoxyphosphinyl]methoxy]prop yl]adenine fumarate Form A. 2θ values in unit of degree in accordance with the abscissa. The intensity of diffraction peak as ordinate.

The XRPD pattern of the resulting crystal Form A is shown in FIG. 4 and information of diffraction peaks at 2θ values was list in the following table:

| 2θ (degree) | d(Å) | I(Height) % |
|---|---|---|
| 4.798 | 18.4005 | 11.6 |
| 5.340 | 16.5356 | 7.8 |
| 8.102 | 10.9037 | 3.2 |
| 8.522 | 10.3677 | 4.8 |
| 9.560 | 9.2437 | 10.9 |
| 9.821 | 8.999 | 29.1 |
| 10.54 | 8.3862 | 59.7 |
| 11.359 | 7.7834 | 7.6 |
| 12.541 | 7.0526 | 3.4 |
| 13.339 | 6.632 | 11.7 |
| 14.020 | 6.3116 | 6.7 |
| 15.061 | 5.8778 | 44.7 |
| 15.702 | 5.6391 | 16.5 |
| 16.200 | 5.4667 | 2.4 |
| 16.960 | 5.2236 | 35.8 |
| 17.640 | 5.0235 | 21.1 |
| 19.000 | 4.6671 | 12.8 |
| 19.540 | 4.5393 | 48.8 |
| 20.780 | 4.271 | 26.7 |
| 21.180 | 4.1913 | 49.5 |
| 21.870 | 4.0607 | 3.6 |
| 22.361 | 3.9726 | 13.1 |
| 23.180 | 3.834 | 38.4 |
| 23.760 | 3.7417 | 100 |
| 25.219 | 3.5284 | 15.6 |
| 25.876 | 3.4404 | 2.2 |
| 26.657 | 3.3413 | 8.6 |
| 27.060 | 3.2924 | 15.9 |
| 28.501 | 3.1291 | 50.9 |
| 30.203 | 2.9566 | 6.1 |
| 30.707 | 2.9092 | 0.8 |
| 31.262 | 2.8588 | 4.5 |
| 32.063 | 2.7892 | 3.2 |
| 32.724 | 2.7344 | 1.8 |
| 33.499 | 2.6728 | 14.6 |
| 36.524 | 2.4581 | 1.4 |
| 39.016 | 2.3066 | 2.7 |
| 41.275 | 2.1855 | 0.8 |

Example 12

50 mg of 9-[(R)-2-[[(S)-[[(S)-1-(isopropoxycarbonyl) ethyl]amino]phenoxyphosphinyl]methoxy]prop yl]adenine freebase was slurried in 1 ml tetrahydrofuran organic solvent and then excessive aliquots of fumaric acid was added and the precipitation was obtained. The precipitation was allowed to be slurried for 24 hours. The XRPD pattern of the obtained Form B is consistent with FIG. 4.

Figure 5:
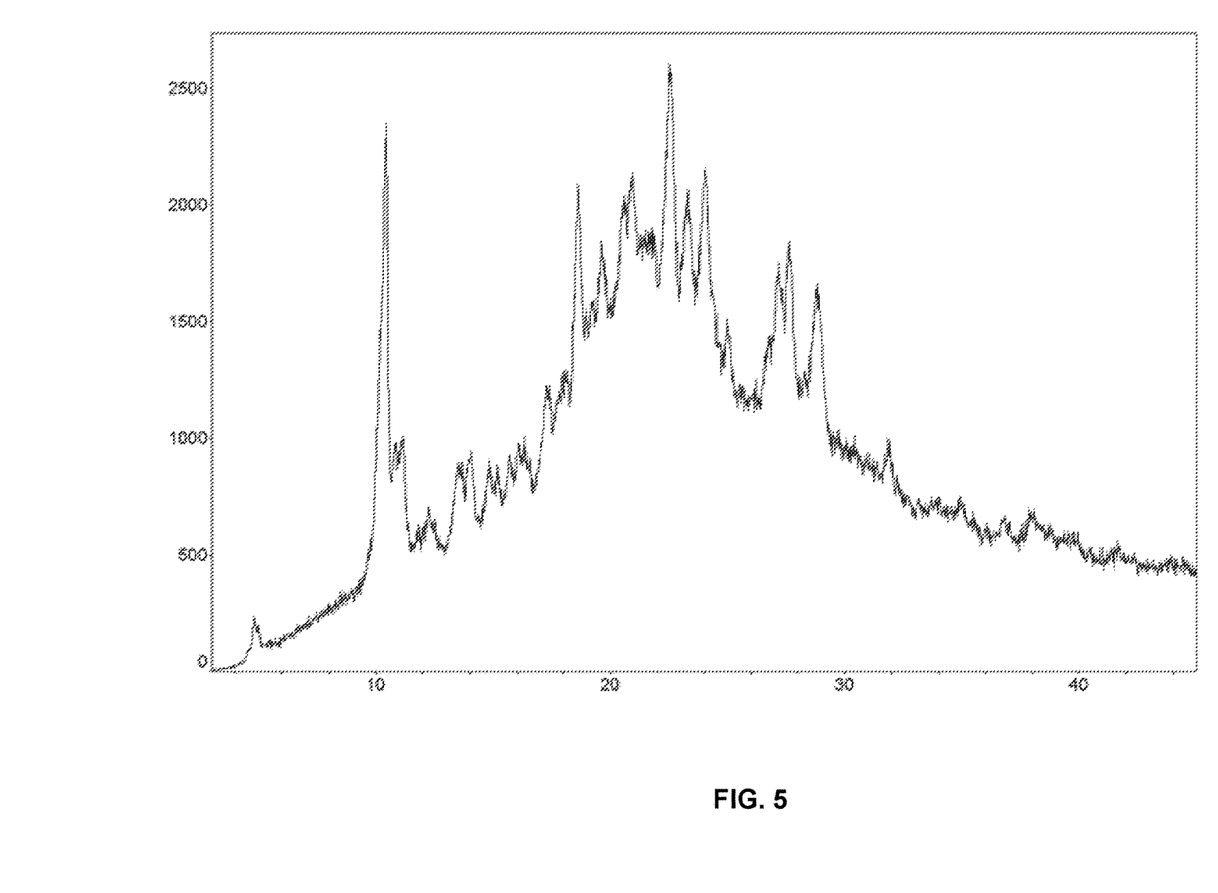
FIG. 5 is an XRPD diffraction pattern of 9-[(R)-2-[[(S)-[[(S)-1-(isopropoxycarbonyl)ethyl]amino]phenoxyphosphinyl]methoxy]prop yl]adenine fumarate Form B. 2θ values in unit of degree in accordance with the abscissa. The intensity of diffraction peak as ordinate.

The XRPD pattern of the resulting crystal Form B is shown in FIG. 5 and information of diffraction peaks at 2θ values was list in the following table:

| 2θ (degree) | d(Å) | I(Height) % |
|---|---|---|
| 4.859 | 18.173 | 15.1 |
| 10.459 | 8.4507 | 100 |
| 10.88 | 8.1254 | 44.6 |
| 11.161 | 7.921 | 13.9 |
| 12.277 | 7.2033 | 7.6 |
| 13.539 | 6.5347 | 19.3 |
| 14.079 | 6.2852 | 14 |
| 14.841 | 5.9643 | 8.6 |
| 15.145 | 5.8451 | 8.6 |
| 15.716 | 5.6341 | 5.6 |
| 16.376 | 5.4083 | 13.7 |
| 17.283 | 5.1265 | 6.6 |
| 18.067 | 4.9059 | 5.1 |
| 18.660 | 4.7513 | 19.4 |
| 19.624 | 4.52 | 9.7 |
| 20.582 | 4.3118 | 18.6 |

-continued

| 2θ (degree) | d(Å) | I(Height) % |
|---|---|---|
| 20.959 | 4.2349 | 44.8 |
| 21.822 | 4.0695 | 4.5 |
| 22.540 | 3.9414 | 37.9 |
| 23.319 | 3.8115 | 12.4 |
| 24.079 | 3.6929 | 24.8 |
| 27.200 | 3.2757 | 41.5 |
| 27.659 | 3.2225 | 29.1 |
| 28.860 | 3.0911 | 30.1 |
| 31.845 | 2.8078 | 4.5 |
| 35.017 | 2.5603 | 4.3 |
| 36.834 | 2.4381 | 3.6 |
| 37.959 | 2.3684 | 7.1 |
| 39.954 | 2.2546 | 3.8 |
| 41.697 | 2.1643 | 4 |
| 43.903 | 2.0605 | 3.2 |

Example 13

Study on the stability of compatibility of different crystalline forms of TAF fumarate with emtricitabine. In this patent, TAF fumarate crystal form I (prepared according to the method of WO2013025788A1), TAF fumarate crystal form II, TAF fumarate crystal form A and TAF fumarate crystal form B and emtricitabine are compared. The mixture was mixed at a weight ratio of about 1:15, placed at 40° C. and a relative humidity of 75%, and placed open for 21 days. The degradation of TAF was analyzed by HPLC at 0 days and 21 day. The results are shown in the following table. Shown as follows:

| Samples | TAF total degradation impurities % | |
|---|---|---|
| | 0 day | 21 day |
| TAF fumarate Form I | 0.1% | 0.9% |
| TAF fumarate Form I + emtricitabine | 0.1% | 3.1% |
| TAF fumarate Form II + emtricitabine | 0.1% | 2.0% |
| TAF fumarate Form A + emtricitabine | 0.1% | 1.0% |
| TAF fumarate Form B + emtricitabine | 0.1% | 1.3% |

The invention claimed is:

1. A crystalline form of 9-[(R)-2-[[(S)-[[(S)-1-(isopropoxycarbonyl)ethyl]amino]phenoxyphosphinyl]methoxy]propyl]adenine fumarate designated as crystalline form A, having an X-ray powder diffraction pattern comprising diffraction peaks at at least one 2θ value of: 23.8±0.2, 10.5±0.2, 28.5±0.2, 21.2±0.2, or 19.5±0.2.

2. A process for the preparation of 9-[(R)-2-[[(S)-[[(S)-1-(isopropoxycarbonyl)ethyl]amino]phenoxyphosphinyl]methoxy]propyl]adenine fumarate crystalline form A according to claim 1, comprising:
(i) dissolving 9-[(R)-2-[[(S)-[[(S)-1-(isopropoxycarbonyl)ethyl]amino]phenoxyphosphinyl]methoxy]propyl]adenine free base in an organic solution;
(ii) adding a fumaric acid in a molar amount no less than the free base into the solution prepared in the step (i) to precipitate a 9-[(R)-2-[[(S)-[[(S)-1-(isopropoxycarbonyl)ethyl]amino]phenoxyphosphinyl]methoxy]propyl]adenine fumarate salt; and
(iii) obtaining 9-[(R)-2-[[(S)-[[(S)-1-(isopropoxycarbonyl)ethyl]amino]phenoxyphosphinyl]methoxy]propyl]adenine fumarate crystalline form A after liquid-solid separation.

3. A crystalline form of 9-[(R)-2-[[(S)-[[(S)-1-(isopropoxycarbonyl)ethyl]amino]phenoxyphosphinyl]methoxy]propyl]adenine fumarate designated as crystalline form B, having an X-ray powder diffraction pattern comprising diffraction peaks at at least one 2θ value of: 10.5±0.2, 21.0±0.2, 10.9±0.2, 27.2±0.2, or 22.5±0.2.

4. A process for the preparation of 9-[(R)-2-[[(S)-[[(S)-1-(isopropoxycarbonyl)ethyl]amino]phenoxyphosphinyl]methoxy]propyl]adenine fumarate crystalline form B according to claim 3, comprising:
(i) dissolving 9-[(R)-2-[[(S)-[[(S)-1-(isopropoxycarbonyl)ethyl]amino]phenoxyphosphinyl]methoxy]propyl]adenine free base in an organic solution;
(ii) adding a fumaric acid in a molar amount greater than the free base into the solution prepared in the step (i) to precipitate a 9-[(R)-2-[[(S)-[[(S)-1-(isopropoxycarbonyl)ethyl]amino]phenoxyphosphinyl]methoxy]propyl]adenine fumarate salt; and
(iii) obtaining 9-[(R)-2-[[(S)-[[(S)-1-(isopropoxycarbonyl)ethyl]amino]phenoxyphosphinyl]methoxy]propyl]adenine fumarate crystalline form B after liquid-solid separation.

5. A crystalline form of 9-[(R)-2-[[(S)-[[(S)-1-(isopropoxycarbonyl)ethyl]amino]phenoxyphosphinyl]methoxy]propyl]adenine fumarate designated as crystalline form II, having an X-ray powder diffraction pattern comprising diffraction peaks at at least one 2θ value of: 26.6±0.2, 21.3±0.2, 27.1±0.2, 19.6±0.2, or 18.7±0.2.

6. The 9-[(R)-2-[[(S)-[[(S)-1-(isopropoxycarbonyl)ethyl]amino]phenoxyphosphinyl]methoxy]propyl]adenine fumarate crystalline form II according to claim 5 having a melting point of 106.6±2° C.

7. A process for the preparation of 9-[(R)-2-[[(S)-[[(S)-1-(isopropoxycarbonyl)ethyl]amino]phenoxyphosphinyl]methoxy]propyl]adenine fumarate crystalline form II according to claim 5, comprising:
(i) dissolving 9-[(R)-2-[[(S)-[[(S)-1-(isopropoxycarbonyl)ethyl]amino]phenoxyphosphinyl]methoxy]propyl]adenine free base in an organic solution;
(ii) adding a fumaric acid in a molar amount into the solution prepared in the step (i) to precipitate a 9-[(R)-2-[[(S)-[[(S)-1-(isopropoxycarbonyl)ethyl]amino]phenoxyphosphinyl]methoxy]propyl]adenine fumarate salt; and
(iii) obtaining 9-[(R)-2-[[(S)-[[(S)-1-(isopropoxycarbonyl)ethyl]amino]phenoxyphosphinyl]methoxy]propyl]adenine fumarate crystalline form II after liquid-solid separation.

8. The 9-[(R)-2-[[(S)-[[(S)-1-(isopropoxycarbonyl)ethyl]amino]phenoxyphosphinyl]methoxy]propyl]adenine fumarate crystalline form A according to claim 1, wherein the X-ray powder diffraction pattern further comprises diffraction peaks at at least one 2θ value of: 15.1±0.2, 23.2±0.2, 17.0±0.2, 9.8±0.2, 20.8±0.2, or 17.6±0.2.

9. The 9-[(R)-2-[[(S)-[[(S)-1-(isopropoxycarbonyl)ethyl]amino]phenoxyphosphinyl]methoxy]propyl]adenine fumarate crystalline form A according to claim 1, wherein the X-ray powder diffraction pattern further comprises diffraction peaks at at least one 2θ value of: 15.7±0.2, 27.1±0.2, 25.2±0.2, 33.5±0.2, 22.4±0.2, or 19.0±0.2.

10. The 9-[(R)-2-[[(S)-[[(S)-1-(isopropoxycarbonyl)ethyl]amino]phenoxyphosphinyl]methoxy]propyl]adenine fumarate crystalline form A according to claim 1, wherein the X-ray powder diffraction pattern further comprises diffraction peaks at at least one 2θ value of: 13.3±0.2, 4.8±0.2, 9.6±0.2, 26.7±0.2, 5.3±0.2, 11.4±0.2, 14.0±0.2, 30.2±0.2, 8.5±0.2, 31.3±0.2, 21.9±0.2, or 12.5±0.2.

11. The 9-[(R)-2-[[(S)-[[(S)-1-(isopropoxycarbonyl)ethyl]amino]phenoxyphosphinyl]methoxy]propyl]adenine fumarate crystalline form B according to claim 3, wherein the X-ray powder diffraction pattern further comprises diffraction peaks at at least one 2θ value of: 28.9±0.2, 27.7±0.2, 24.1±0.2, 18.7±0.2, 13.5±0.2, or 20.6±0.2.

12. The 9-[(R)-2-[[(S)-[[(S)-1-(isopropoxycarbonyl)ethyl]amino]phenoxyphosphinyl]methoxy]propyl]adenine fumarate crystalline form B according to claim 3, wherein the X-ray powder diffraction pattern further comprises diffraction peaks at at least one 2θ value of: 4.9±0.2, 14.1±0.2, 11.2±0.2, 16.4±0.2, 23.3±0.2, or 19.6±0.2.

13. The 9-[(R)-2-[[(S)-[[(S)-1-(isopropoxycarbonyl)ethyl]amino]phenoxyphosphinyl]methoxy]propyl]adenine fumarate crystalline form B according to claim 3, wherein the X-ray powder diffraction pattern further comprises diffraction peaks at at least one 2θ value of: 11.8±0.2, 15.1±0.2, 12.3±0.2, 38.0±0.2, 17.3±0.2, 15.7±0.2, 18.1±0.2, 21.8±0.2, 31.8±0.2, 35.0±0.2, 41.7±0.2, or 40.0±0.2.

14. The 9-[(R)-2-[[(S)-[[(S)-1-(isopropoxycarbonyl)ethyl]amino]phenoxyphosphinyl]methoxy]propyl]adenine fumarate crystalline form II according to claim 5, wherein the X-ray powder diffraction pattern further comprises diffraction peaks at at least one 2θ value of: 32.1±0.2, 21.9±0.2, 5.4±0.2, 22.4±0.2, 11.1±0.2, or 17.8±0.2.

15. The 9-[(R)-2-[[(S)-[[(S)-1-(isopropoxycarbonyl)ethyl]amino]phenoxyphosphinyl]methoxy]propyl]adenine fumarate crystalline form II according to claim 5, wherein the X-ray powder diffraction pattern further comprises diffraction peaks at at least one 2θ value of: 12.9±0.2, 24.5±0.2, 24.9±0.2, 19.0±0.2, 23.6±0.2, or 30.0±0.2.

16. The 9-[(R)-2-[[(S)-[[(S)-1-(isopropoxycarbonyl)ethyl]amino]phenoxyphosphinyl]methoxy]propyl]adenine fumarate crystalline form II according to claim 5, wherein the X-ray powder diffraction pattern further comprises diffraction peaks at at least one 2θ value of: 32.4±0.2, 37.5±0.2, 10.5±0.2, 14.5±0.2, 16.7±0.2, or 40.3±0.2.

17. The 9-[(R)-2-[[(S)-[[(S)-1-(isopropoxycarbonyl)ethyl]amino]phenoxyphosphinyl]methoxy]propyl]adenine fumarate crystalline form II according to claim 5, wherein the X-ray powder diffraction pattern further comprises diffraction peaks at at least one 2θ value of: 23.9±0.2, 12.3±0.2, 38.6±0.2, 43.0±0.2, 27.8±0.2, or 35.8±0.2.

18. A pharmaceutical composition comprising the 9-[(R)-2-[[(S)-[[(S)-1-(isopropoxycarbonyl)ethyl]amino]phenoxyphosphinyl]methoxy]propyl]adenine fumarate crystalline form A according to claim 1 as an active ingredient to treat hepatitis B virus (HBV) infection or human immunodeficiency virus (HIV) infection.

19. A pharmaceutical composition comprising the 9-[(R)-2-[[(S)-[[(S)-1-(isopropoxycarbonyl)ethyl]amino]phenoxyphosphinyl]methoxy]propyl]adenine fumarate crystalline form B according to claim 3 as an active ingredient to treat hepatitis B virus (HBV) infection or human immunodeficiency virus (HIV) infection.

20. A pharmaceutical composition comprising the 9-[(R)-2-[[(S)-[[(S)-1-(isopropoxycarbonyl)ethyl]amino]phenoxyphosphinyl]methoxy]propyl]adenine fumarate crystalline form II according to claim 5 as an active ingredient to treat hepatitis B virus (HBV) infection or human immunodeficiency virus (HIV) infection.

* * * * *